US012691256B2

(12) United States Patent
Avivi et al.

(10) Patent No.: US 12,691,256 B2
(45) Date of Patent: Jul. 28, 2026

(54) STEERABLE MEDICAL DEVICE, HANDLE FOR A MEDICAL DEVICE, AND METHOD FOR OPERATING A MEDICAL DEVICE

(71) Applicant: Boston Scientific Medical Device Limited, Galway (IE)

(72) Inventors: Doran Avivi, Toronto (CA); Jan-Hung Chen, Georgetown (CA)

(73) Assignee: Boston Scientific Medical Device Limited, Galway (IE)

( * ) Notice: Subject to any disclaimer, the term of this patent is extended or adjusted under 35 U.S.C. 154(b) by 643 days.

(21) Appl. No.: 18/296,583

(22) Filed: Apr. 6, 2023

(65) Prior Publication Data

US 2023/0241351 A1     Aug. 3, 2023

Related U.S. Application Data

(63) Continuation of application No. PCT/IB2021/057651, filed on Aug. 19, 2021.
(Continued)

(51) Int. Cl.
*A61M 25/01*         (2006.01)
*A61B 1/005*         (2006.01)
(52) U.S. Cl.
CPC .... *A61M 25/0136* (2013.01); *A61M 25/0147* (2013.01); *A61B 1/0052* (2013.01)
(58) Field of Classification Search
CPC .......... A61M 25/0136; A61M 25/0147; A61B 1/0052
See application file for complete search history.

(56) References Cited

U.S. PATENT DOCUMENTS 5,545,200 A * 8/1996 West ................. A61M 25/0136
                                                606/29
5,549,542 A * 8/1996 Kovalcheck ......... A61B 1/0052
                                                600/150
(Continued)

FOREIGN PATENT DOCUMENTS

EP         2712538 A1    4/2014
JP      2019509135 A     4/2019
WO      2016175882 A1    11/2016

OTHER PUBLICATIONS

International Search Report for PCT Application No. PCT/IB2021/057651 mailed Nov. 24, 2021.
(Continued)

*Primary Examiner* — Laura A Bouchelle
(74) *Attorney, Agent, or Firm* — Nelson Mullins Riley & Scarborough LLP

(57)              ABSTRACT

A steerable medical device includes a handle having a handle body and a knob that is rotatable about a knob axis with respect to the handle body. An elongate tool extends from the handle. A steering assembly causes deflection of the tool by rotation of the knob. The steering assembly includes a slider that is housed within the handle body and is translatable within the handle body. The steering assembly further includes a control wire coupled between the slider and the tool. Translation of the slider causes tensioning of the control wire and tensioning of the control wire causes deflection of the tool. The steering assembly further includes a crank assembly coupled between the knob and the slider, to drive translation of the slider by rotation of the knob.

16 Claims, 3 Drawing Sheets

Related U.S. Application Data

(60) Provisional application No. 63/087,917, filed on Oct. 6, 2020.

(56) References Cited

U.S. PATENT DOCUMENTS

| | | | |
|---|---|---|---|
| 7,465,288 B2 * | 12/2008 | Dudney | A61M 25/0136 |
| | | | 604/95.04 |
| 2003/0191516 A1 | 10/2003 | Weldon et al. | |
| 2016/0089125 A1 | 3/2016 | Morimoto | |
| 2019/0089125 A1 | 3/2019 | Eichler et al. | |

OTHER PUBLICATIONS

International Preliminary Report on Patentability received for PCT Patent Application No. PCT/IB2021/057651, mailed on Apr. 20, 2023, 08 pages.

* cited by examiner

STEERABLE MEDICAL DEVICE, HANDLE FOR A MEDICAL DEVICE, AND METHOD FOR OPERATING A MEDICAL DEVICE

CROSS-REFERENCE TO RELATED APPLICATIONS

This application is a continuation of and claims the benefit of International Application Number PCT/IB2021/057651, entitled "STEERABLE MEDICAL DEVICE, HANDLE FOR A MEDICAL DEVICE, AND METHOD FOR OPER-ATING A MEDICAL DEVICE," and filed Aug. 19, 2021, which claims the benefit of U.S. Provisional Application No. 63/087,917, entitled "STEERABLE MEDICAL DEVICE, HANDLE FOR A MEDICAL DEVICE, AND METHOD FOR OPERATING A MEDICAL DEVICE," and filed Oct. 6, 2020, which are hereby incorporated by reference in their entireties.

FIELD

This document relates to medical devices. More specifi-cally, this document relates to steerable medical devices such as steerable sheaths, catheters, and introducers.

SUMMARY

The following summary is intended to introduce the reader to various aspects of the detailed description, but not to define or delimit any invention.

Steerable medical devices are disclosed. According to some aspects, a steerable medical device includes a handle having a handle body and a knob that is rotatable about a knob axis with respect to the handle body. An elongate tool extends from the handle. A steering assembly causes deflec-tion of the tool by rotation of the knob. The steering assembly includes a slider that is housed within the handle body and that is translatable within the handle body, a control wire that is coupled between the slider and the tool, so that translation of the slider causes tensioning of the control wire and tensioning of the control wire causes deflection of the tool, and a crank assembly coupled between the knob and the slider to drive translation of the slider by rotation of the knob.

In some examples, the crank assembly includes a shaft that is coupled to the knob and is rotatable with the knob about the knob axis. The crank assembly can further include a crank that is coupled to the shaft and is pivotable about the knob axis by rotation of the shaft. The crank can have a fixed end that is fixed to the shaft, and a free end that is spaced from the fixed end and that orbits the shaft. The crank assembly can further include a connecting rod coupled between the slider and the free end of the crank. Pivoting of the crank about the knob axis can drive rotation and trans-lation of the connecting rod, and rotation and translation of the connecting rod can drive translation of the slider.

In some examples, the connecting rod can have a first end that is pivotably coupled to the free end of the crank and a second end that is pivotably coupled to the slider.

In some examples, the slider is mounted to a track that limits movement of the slider.

In some examples, the crank assembly further includes a pinion gear that is rotatably mounted to the connecting rod, and a first rack that is engaged with the pinion gear and fixed in position. The slider can include a second rack that is engaged with the pinion gear.

In some examples, the tool is a sheath, a catheter, or an introducer.

According to some aspects, a handle for a medical device includes a handle body and a knob that is rotatable about a knob axis with respect to the handle body. A slider is housed within the handle body and is translatable within the handle body. A control wire is coupled to slider. Translation of the slider causes tensioning of the control wire. A crank assem-bly is coupled between the knob and the slider to drive translation of the slider by rotation of the knob.

In some examples, the crank assembly includes a shaft that is coupled to the knob and is rotatable with the knob about the knob axis. The crank assembly can further include a crank that is coupled to the shaft and is pivotable about the knob axis by rotation of the shaft. The crank can have a fixed end that is fixed to the shaft, and a free end that is spaced from the fixed end and that orbits the shaft. A connecting rod can be coupled between the slider and the free end of the crank. Pivoting of the crank about the knob axis can drive rotation and translation of the connecting rod, and rotation and translation of the connecting rod can drive translation of the slider.

In some examples, the connecting rod has a first end that is pivotably coupled to the free end of the crank and a second end that is pivotably coupled to the slider.

In some examples, the slider is mounted to a track that limits movement of the slider.

In some examples, the crank assembly further includes a pinion gear that is rotatably coupled to the connecting rod, and first rack that is engaged with the pinion gear and fixed in position. The slider can include a second rack that is engaged with the pinion gear.

Methods for operating a medical device are also dis-closed. According to some aspects, a method for operating a medical device includes: a. rotating a knob of a handle of the medical device to drive movement a crank assembly housed within the handle; b. driving translation of a slider by movement of the crank assembly; c. tensioning a control wire by translation of the slider; and d. deflecting a tool coupled to the handle by tensioning of the control wire.

In some examples, rotation of the knob drives rotation of a shaft of the crank assembly. Rotation of the shaft can drive pivoting of a crank of the crank assembly. Pivoting of the crank can drive rotation and translation of a connecting rod. Rotation and translation of the connecting rod can drive of the slider.

BRIEF DESCRIPTION OF THE DRAWINGS

The accompanying drawings are for illustrating examples of articles, methods, and apparatuses of the present disclo-sure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are steerable medical devices that include a handle and a tool such as a sheath, a catheter, or an introducer. The handle can enable the user to manipulate or steer the tool in a desired direction. More specifically, the handle can include a knob that is rotatably coupled to a housing (also referred to as a 'body') of the handle. In operation, rotation of the knob can allow the user to steer or deflect the tool. Rotation of the knob can be converted into deflection of the tool via a crank assembly and one or more sliders, which can be within the housing, and one or more control wires, which can be coupled between the slider(s) and the tool. Rotation of the knob can cause movement of the crank assembly, and movement of the crank assembly can cause translation of the slider(s). Translation of the slider(s) can cause tensioning of the control wire(s), which results in deflection of the tool. For simplicity, details of the control wire(s) and the connection between the control wire(s), the tool, and the slider(s) are not disclosed herein. However, related sliders and control wires are disclosed in, for example, U.S. Pat. No. 10,661,057 (Davies et al.), which is incorporated herein by reference in its entirety. Furthermore, steerable medical devices including sliders and control wires are sold Baylis Medical Company, Inc. (Montreal, Canada) under the brand name SureFlex® Steerable Guiding Sheath.

Figure 1:
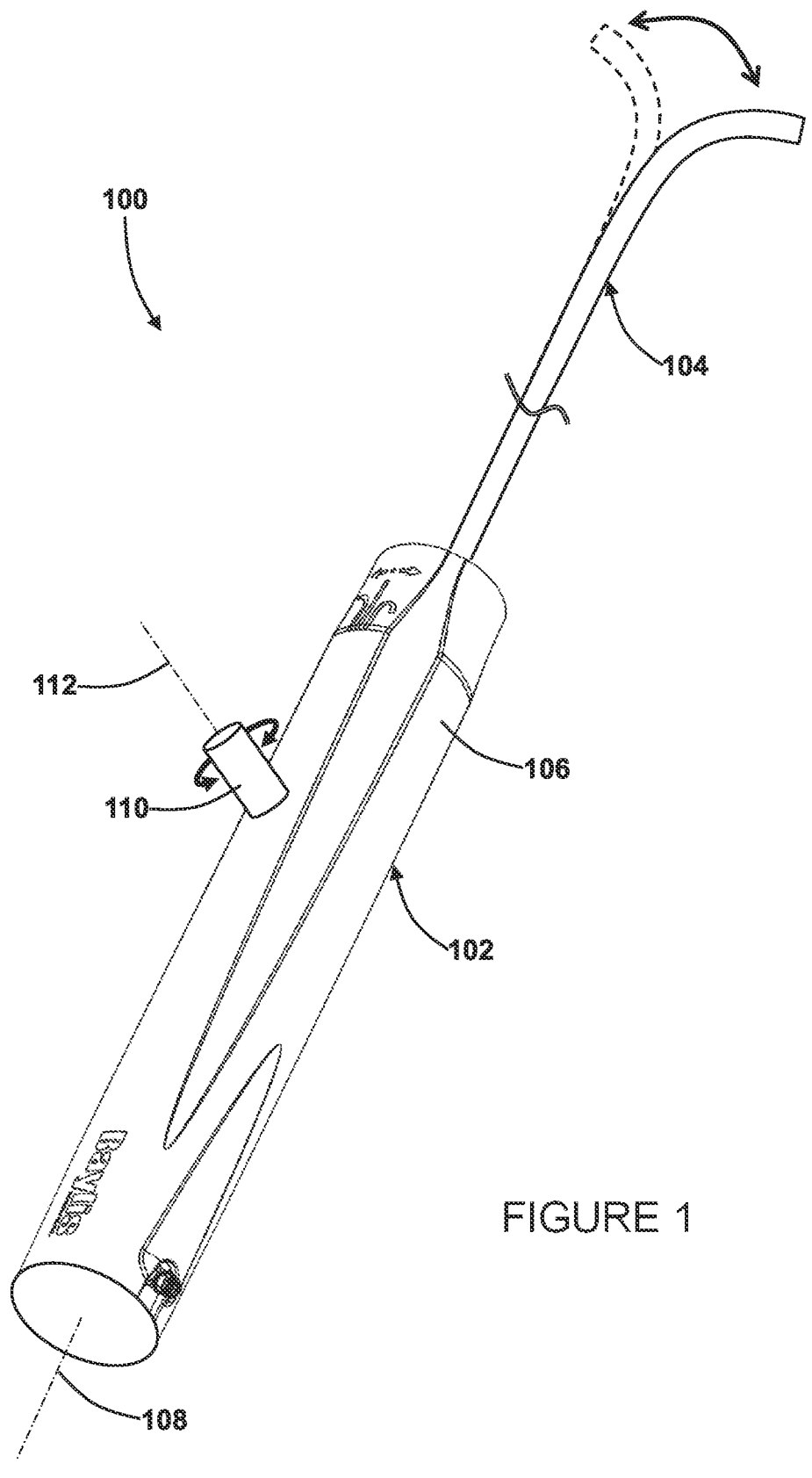
FIG. 1 is a perspective view of an example steerable medical device.

Referring now to FIG. 1, an example steerable medical device 100 is shown. The steerable medical device 100 generally includes a handle 102 and an elongate tool 104 extending from the handle. The tool 104 can be, for example (but not limited to), a sheath, a catheter, or an introducer.

Referring still to FIG. 1, the handle 102 includes a handle body 106 (also referred to as a housing), which extends along a handle axis 108, and a knob 110 that is rotatable about a knob axis 112 with respect to the handle body 106. In the example shown, the knob axis 112 is perpendicular to the handle axis 108. In alternative examples, the knob can be rotatable about a knob axis that is parallel to the handle axis, or at another orientation with respect to the handle axis.

Referring still to FIG. 1, in the example shown, rotation of the knob 110 in a first rotational direction (e.g. clockwise) can cause the tool 104 to deflect in a first deflectional direction (i.e. to the configuration shown in solid line in FIG.

1), and rotation of the knob 110 in a second rotational direction (e.g. counter-clockwise) can cause the tool 104 to deflect in a second deflectional direction (i.e. to the configuration shown in dotted line in FIG. 1).

Figures 2, 3, 4:
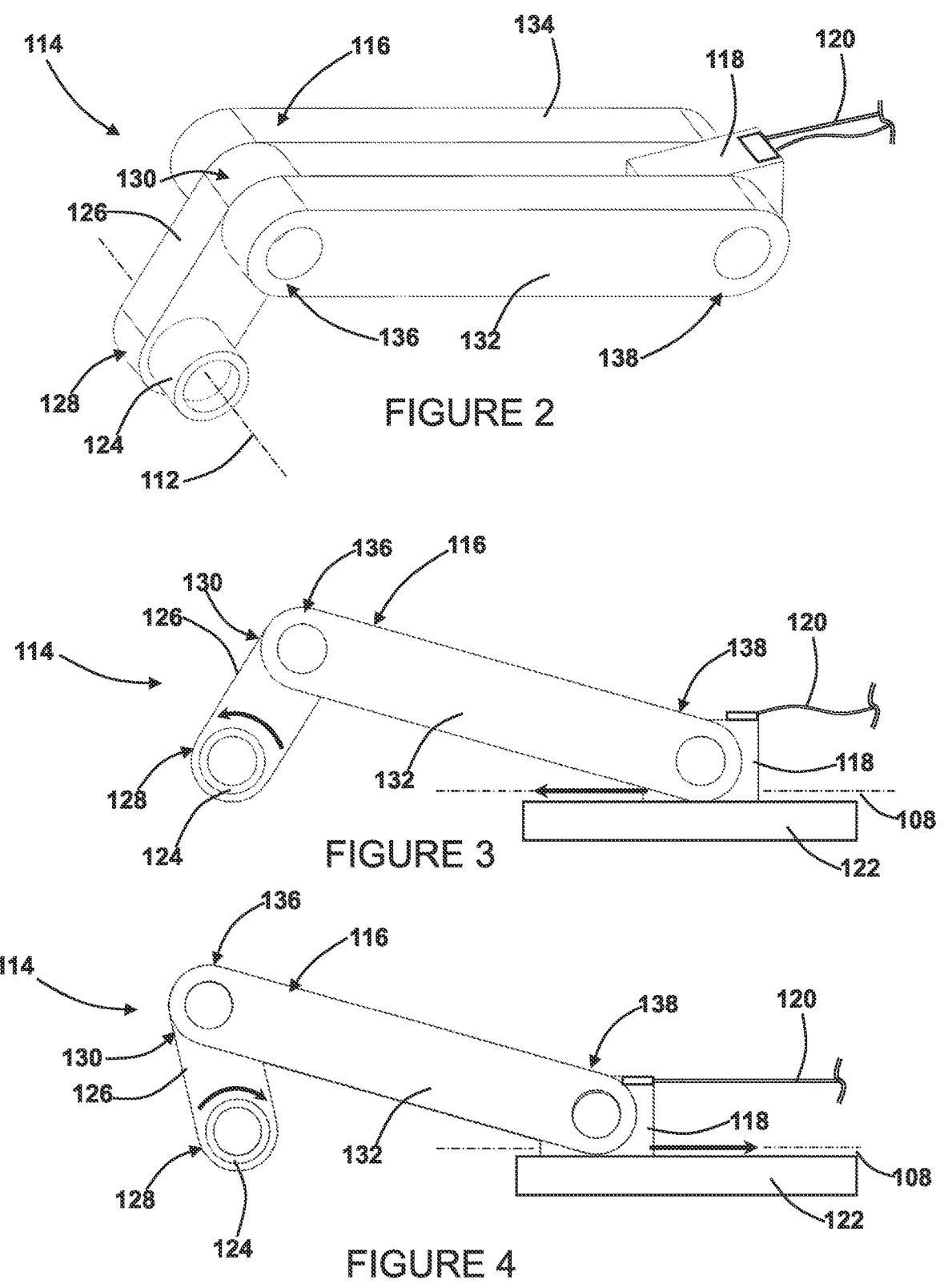
FIG. 2 is a perspective view of a steering assembly of the medical device of FIG. 1.
FIG. 3 is a side view of the steering assembly of FIG. 2, showing the steering assembly in a first position.
FIG. 4 is a side view of the steering assembly of FIG. 2, showing the steering assembly in a second position.

Referring to FIG. 2, a steering assembly 114 is provided for causing deflection of the tool 104 (not shown in FIG. 2) by rotation of the knob 110 (not shown in FIG. 2). In the example shown, the steering assembly 114 generally includes a crank assembly 116 that is housed in the handle body 106 (not shown in FIG. 2), a slider 118 that is housed in the handle body 106, and a control wire 120.

Referring to FIGS. 3 and 4, the slider 118 is translatable within the handle body 106 (not shown in FIGS. 3 and 4), along the handle axis 108. That is, the slider 118 is translatable proximally (i.e. towards the left of the page in FIGS. 3 and 4) and distally (i.e. towards the right of the page in FIGS. 3 and 4) within the handle body 106, between the positions shown in FIGS. 3 and 4. The slider 118 is mounted to a track 122, which limits movement of the slider 118 to translation along the handle axis 108, and prevents movement in other directions (e.g. prevents movement perpendicular to the handle axis 108).

Referring still to FIGS. 3 and 4, the control wire 120 is coupled between the slider 118 and the tool 104 (not shown in FIGS. 2 to 4). Translation of the slider 118 causes tensioning of the control wire 120, and tensioning of the control wire 120 causes deflection of the tool 104 (as noted above, the control wire 120 and the connection between the control wire 120, the tool 104, and the slider 118 are shown schematically in the Figures, and the details thereof are not disclosed herein).

Referring still to FIGS. 2 to 4, the crank assembly 116 is coupled between the knob 110 (not shown in FIGS. 2 to 4) and the slider 118, to drive translation of the slider 118 by rotation of the knob 110. In the example shown, the crank assembly 116 includes a shaft 124 that is coupled to the knob 110 (e.g. fixed to the knob 110 via an opening in the handle body 106) and that is rotatable with the knob 110 about the knob axis 112. The crank assembly 116 further includes a crank 126 that is coupled to the shaft 124 and is pivotable about the knob axis 112 by rotation of the shaft 124. In the example shown, the crank 126 has a fixed end 128 that is fixed to the shaft 124, and a free end 130 that is spaced from the fixed end 128 and that orbits the shaft 124. The crank assembly 116 further includes a first connecting rod 132 and a second connecting rod 134, each of which is coupled between the slider 118 and the free end 130 of the crank 126. The first connecting rod 132 has a first end 136 that is pivotably coupled to the free end 130 of the crank 126, and a second end 138 that is pivotably coupled to the slider 118. The second connecting rod 134 also has a first end (not shown) that is pivotably coupled to the free end 130 of the crank 126, and a second end (not shown) that is pivotably coupled to the slider 118. Pivoting of the crank 126 about the knob axis 112 drives rotation and translation of the connecting rods 132, 134, and rotation and translation of the connecting rods 132, 134 drives translation of the slider 118. That is, as shown in FIG. 3, rotation of the knob 110 (not shown in FIG. 3) about the knob axis 112 (not shown in FIG. 3) in a counter-clockwise direction causes rotation of the shaft 124 about the knob axis 112 in a counter-clockwise direction; rotation of the shaft 124 about the knob axis 112 in a counter-clockwise direction causes pivoting of the crank 126 in a counter-clockwise direction; pivoting of the crank 126 in the counter-clockwise direction causes rotation and proximal translation of the connecting rods 132, 134; and rotation and proximal translation of the connecting rods 132, 134 causes proximal translation of the slider 118. Similarly, as shown in FIG. 4, rotation of the knob 110 (not shown in FIG. 4) about the knob axis 112 (not shown in FIG. 4) in a clockwise direction causes rotation of the shaft 124 about the knob axis 112 in a clockwise direction; rotation of the shaft 124 about the knob axis 112 in a clockwise direction causes pivoting of the crank 126 in a clockwise direction; pivoting of the crank 126 in the clockwise direction causes rotation and distal translation of the connecting rods 132, 134; and rotation and distal translation of the connecting rods 132 causes proximal translation of the slider 118.

Figures 5, 6, 7:
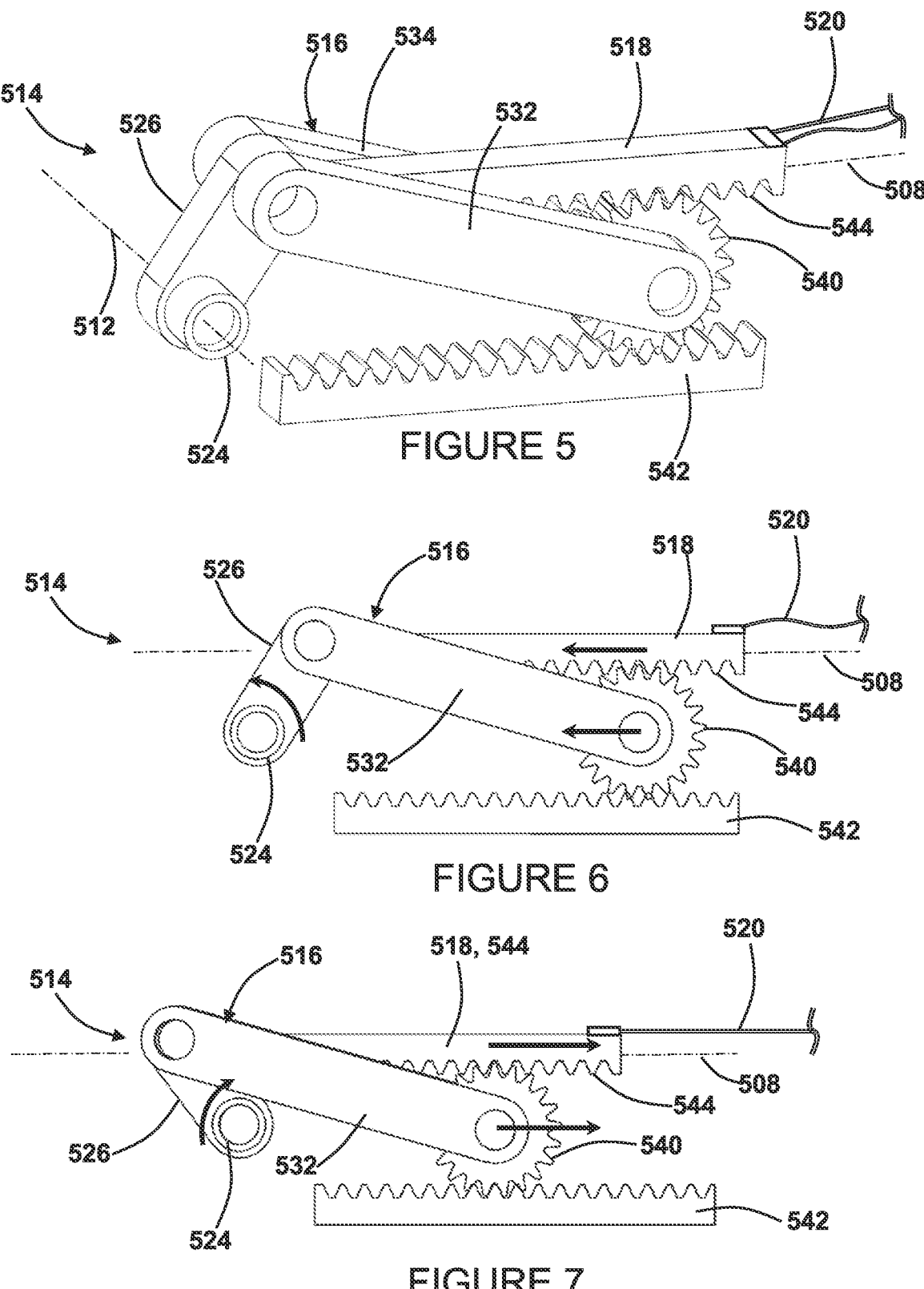
FIG. 5 is a perspective view of another example steering assembly for a medical device
FIG. 6 is a side view of the steering assembly of FIG. 5, showing the steering assembly in a first position.
FIG. 7 is a side view of the steering assembly of FIG. 6, showing the steering assembly in a second position.

Referring now to FIGS. 5 to 7, an alternative example of a steering assembly is shown. In FIGS. 5 to 7, features that are like those of FIGS. 1 to 4 will be referenced with like reference characters, incremented by 400.

Similarly to the example of FIGS. 1 to 4, the steering assembly 514 includes a crank assembly 516 coupled between a knob (not shown) and a slider 518 to drive translation of the slider 518 by rotation of the knob. A control wire 520 is coupled between the slider 518 and a tool (not shown), and translation of the slider 518 causes tensioning of the control wire 520 to cause deflection of the tool. Furthermore, similarly to the crank assembly 116 of FIGS. 1 to 4, the crank assembly 516 includes a shaft 524 that is coupled to the knob and is rotatable with the knob about the knob axis 512 (shown in FIG. 5), a crank 526 that is coupled to the shaft 524 and is pivotable about the knob axis 512 by rotation of the shaft 524, and a pair of connecting rods 532, 534 that are coupled between the slider 518 and the crank 526; however the crank assembly 516 of FIGS. 5 to 7 further includes a pinion gear 540 that is rotatably mounted to the second ends of the connecting rods 532, 534, and a first rack 542 that is engaged with the pinion gear 540. The first rack 542 is fixed in position with respect to the handle body (not shown). Furthermore, the slider 518 includes a second rack 544 that is engaged with the pinion gear 540 and that is translatable along the handle axis 508. The second rack 544 can be mounted to a track (not shown), which cam limit movement of the slider 518 to translation along the handle axis 508.

In use, as shown in FIG. 6, rotation of the knob (not shown) about the knob axis 512 (shown in FIG. 5) in a counter-clockwise direction causes rotation of the shaft 524 about the knob axis 512 in a counter-clockwise direction; rotation of the shaft 524 about the knob axis 512 in a counter-clockwise direction causes pivoting of the crank 526 in a counter-clockwise direction; pivoting of the crank 526 in the counter-clockwise direction causes rotation and proximal translation the connecting rods 532, 534; and rotation and proximal translation of the connecting rods 532, 534 causes proximal movement of the pinion gear 540 along the first rack 542. Proximal movement of the pinion gear 540 in turn causes proximal sliding of the second rack 544. Furthermore, as shown in FIG. 7, rotation of the knob (not shown) about the knob axis 512 (shown in FIG. 5) in a clockwise direction causes rotation of the shaft 524 about the knob axis 512 in a clockwise direction; rotation of the shaft 524 about the knob axis 512 in the clockwise direction causes pivoting of the crank 526 in a clockwise direction; pivoting of the crank 526 in the clockwise direction causes rotation and distal translation the connecting rods 532, 534; and rotation and distal translation of the connecting rods 532, 534 causes distal movement of the pinion gear 540 along the first rack 542. Distal movement of the pinion gear 540 in turn causes distal sliding of the second rack 544.

In any of the above examples, the steering assembly may be of another configuration. For example, the crank assembly may include only a single connecting rod; the steering assembly may include more than one control wire; and/or the rack and pinion assembly may be replaced by another type of geared assembly.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A steerable medical device comprising:
a handle having a handle body and a knob that is rotatable about a knob axis with respect to the handle body;
an elongate tool extending from the handle; and
a steering assembly for causing deflection of the tool by rotation of the knob, the steering assembly comprising a slider housed within the handle body and translatable within the handle body, a control wire coupled between the slider and the tool, and a crank assembly coupled between the knob and the slider to drive translation of the slider by rotation of the knob, the crank assembly comprising a shaft coupled to the knob and rotatable with the knob about the knob axis, a crank coupled to the shaft and pivotable about the knob axis by rotation of the shaft, the crank having a fixed end that is fixed to the shaft, and a free end that is spaced from the fixed end and that orbits the shaft, and a first connecting rod and a second connecting rod coupled to the free end of the crank;
whereby translation of the slider causes tensioning of the control wire and tensioning of the control wire causes deflection of the tool.

2. The steerable medical device of claim 1, wherein the first connecting rod and the second connecting rod are coupled between the slider and the free end of the crank, whereby pivoting of the crank about the knob axis drives rotation and translation of the first connecting rod and the second connecting rod, and rotation and translation of the first connecting rod and the second connecting rod drives translation of the slider.

3. The steerable medical device of claim 2, wherein the first connecting rod and the second connecting rod include a first end that is pivotably coupled to the free end of the crank and a second end that is pivotably coupled to the slider.

4. The steerable medical device of claim 3, wherein the slider is mounted to a track that limits movement of the slider.

5. The steerable medical device of claim 2, wherein the crank assembly further comprises a pinion gear rotatably mounted to the first connecting rod and the second connecting rod, and a first rack that is engaged with the pinion gear and fixed in position.

6. The steerable medical device of claim 5, wherein the slider comprises a second rack that is engaged with the pinion gear.

7. The steerable medical device of claim 1, wherein the tool is a sheath, a catheter, or an introducer.

8. A handle for a medical device, the handle comprising:

a handle body;

a knob that is rotatable about a knob axis with respect to the handle body;

a slider housed within the handle body and translatable within the handle body, a control wire coupled to slider, and a crank assembly coupled between the knob and the slider to drive translation of the slider by rotation of the knob, the crank assembly comprising a shaft coupled to the knob and rotatable with the knob about the knob axis, a crank coupled to the shaft and pivotable about the knob axis by rotation of the shaft, the crank having a fixed end that is fixed to the shaft, and a free end that is spaced from the fixed end and that orbits the shaft, and a first connecting rod and a second connecting rod coupled to the free end of the crank;

whereby translation of the slider causes tensioning of the control wire.

9. The steerable medical device of claim 8, wherein the first connecting rod and the second connecting rod are coupled between the slider and the free end of the crank, whereby pivoting of the crank about the knob axis drives rotation and translation of the first connecting rod and the second connecting rod, and rotation and translation of the first connecting rod and the second connecting rod drives translation of the slider.

10. The handle of claim 9, wherein the first connecting rod and the second connecting rod include has a first end that is pivotably coupled to the free end of the crank and a second end that is pivotably coupled to the slider.

11. The handle of claim 9, wherein the crank assembly further comprises a pinion gear rotatably mounted to the first connecting rod and the second connecting rod, and a first rack that is engaged with the pinion gear and fixed in position.

12. The handle of claim 11, wherein the slider comprises a second rack that is engaged with the pinion gear.

13. The handle of claim 8, wherein the slider is fixed in a channel and translatable within the channel.

14. A handle for a medical device, the handle comprising:

a handle body;

a knob that is rotatable about a knob axis with respect to the handle body;

a slider housed within the handle body and translatable within the handle body, a control wire coupled to slider, and a crank assembly coupled between the knob and the slider to drive translation of the slider by rotation of the knob, the crank assembly comprising a shaft coupled to the knob and rotatable with the knob about the knob axis, a crank coupled to the shaft and pivotable about the knob axis by rotation of the shaft, the crank having a fixed end that is fixed to the shaft, and a free end that is spaced from the fixed end and that orbits the shaft, a connecting rod coupled between the slider and the free end of the crank, whereby pivoting of the crank about the knob axis drives rotation and translation of the connecting rod, and rotation and translation of the connecting rod drives translation of the slider, and a pinion gear rotatably coupled to the connecting rod, and first rack that is engaged with the pinion and fixed in position;

whereby translation of the slider causes tensioning of the control wire.

15. The handle of claim 14, wherein the slider comprises a second rack that is engaged with the pinion gear.

16. The handle of claim 14, wherein the slider is fixed in a channel and translatable within the channel.

* * * * *